United States Patent [19]

Shum

[11] Patent Number: 5,278,070
[45] Date of Patent: Jan. 11, 1994

[54] PROCESS FOR PRODUCING EPOXYALCOHOLS OF HIGH OPTICAL PURITY

[75] Inventor: Wilfred P. Shum, West Chester, Pa.

[73] Assignee: Arco Chemical Technology, L.P., Wilmington, Del.

[21] Appl. No.: 863,577

[22] Filed: Apr. 3, 1992

Related U.S. Application Data

[63] Continuation of Ser. No. 516,001, Apr. 26, 1990, abandoned.

[51] Int. Cl.$^5$ .............................................. C12P 41/00
[52] U.S. Cl. ..................................................... 435/280
[58] Field of Search ......................................... 435/280

[56] References Cited

U.S. PATENT DOCUMENTS

| | | | |
|---|---|---|---|
| 4,471,130 | 9/1984 | Katsuki et al. | 549/523 |
| 4,594,439 | 6/1986 | Katsuki et al. | 549/523 |
| 4,732,853 | 3/1988 | Whitesides et al. | 435/280 X |
| 4,764,628 | 8/1988 | Shum | 549/529 |
| 4,916,074 | 4/1990 | Yoshida et al. | 435/280 |
| 4,923,810 | 5/1990 | Walts et al. | 435/117 |
| 5,213,975 | 5/1993 | Fukusaki et al. | 435/123 |

FOREIGN PATENT DOCUMENTS

| | | | |
|---|---|---|---|
| 70618 | 1/1983 | European Pat. Off. | |
| 0197766 | 10/1986 | European Pat. Off. | C07D 303/14 |
| 255379 | 2/1988 | European Pat. Off. | |
| 357009 | 3/1990 | European Pat. Off. | |

OTHER PUBLICATIONS

Okumura S, BBA 575:156-165 (1979).
Zaks A, Science 224:1249-51 (1984).
Bevinakatti H, J. Org. Chem 54:2453-55 (1989).
Kirchner et al., *J. Am. Chem. Soc.* 107, 7072 (1985).
Chen et al., *Angew. Chem. Int. Ed. Engl.* 28, 695 (1989).
Iwai, *Yushi.* 42, 88 (1989).
[Baba et al., *Agric. Biol. Chem.* 52, 2688 (1988)].
Bianchi et al [Tetrahedron Letter 29(20), 2455 (1988)].
Wang et al [J. Am. Chem. Soc. 110, 7200 (1988)].
Klibanov [Acc. Chem. Res. 23, 114 (1990)].
Gao et al [J. Am. Chem. Soc. 109 5765 (1987)].
Jorgensen, Chem. Rev. 89, 431 (1989).
Pfenninger, Synthesis 89 (1986).
Katsuki et al. J. Am. Chem. Soc. 102, 5974 (1980).
Sonnet, J. Org. Chem. 52, 3477 (1987).
Okahata et al, Tetrahedron Letter 29(40), 5133 (1988).
Langrand et al Tetrahedron Letter 26(15), 1857, (1985).
Terao et al, Tetrahedron Letters 29(40), 5173 (1988).
Cambou et al, J. Am. Chem. Soc. 106, 2687 (1984).
Francalanci et al, J. Org. Chem. 52, 5079 (1987).
Belan et al, J. Org. Chem. 52, 256 (1987).

*Primary Examiner*—Douglas W. Robinson
*Assistant Examiner*—S. Saucier
*Attorney, Agent, or Firm*—Stephen D. Harper

[57] ABSTRACT

A process for enriching or improving the optical purity of an asymmetric epoxidation reaction mixture is provided wherein the chiral epoxy alcohol enantiomer present in minor amounts is effectively separated from the predominant chiral epoxy alcohol enantiomer. The minor enantiomer is converted to an epoxy ester by stereoselective transesterification using a carboxylic acid derivative such as an enol ester and a lipase enzyme. The desired major chiral epoxy alcohol enantiomer is then recovered or reacted in situ to form a chiral epoxy alcohol derivative.

6 Claims, No Drawings

PROCESS FOR PRODUCING EPOXYALCOHOLS OF HIGH OPTICAL PURITY

This is a continuation of application Ser. No. 07/516,001, filed Apr. 26, 1990, now abandoned.

BACKGROUND OF THE INVENTION

This invention relates to the purification of epoxidation reaction mixtures. In particular, the invention pertains to the recovery of a chiral epoxy alcohol or chiral epoxy alcohol derivative having high optical purity. The transition metal catalyzed epoxidation of ethylenically unsaturated substrates using organic hydroperoxides as oxidants is a well known method for the preparation of epoxides. In one variation of this technology, optically active epoxy alcohols are prepared by reacting unsaturated alcohols with organic hydroperoxides in the presence of transition metal catalysts containing chiral ligands. The optically active epoxy alcohol products are of great value as intermediates in the synthesis of compounds having high physiological activity.

However, the recovery of pure epoxy alcohols from crude epoxidation reaction mixtures is complicated by the numerous components typically present in such mixtures. The reaction mixture will normally contain a major amount of a first chiral epoxy alcohol, a minor amount of a second chiral epoxy alcohol which is an enantiomer of the first chiral epoxy alcohol, unreacted organic hydroperoxide, unreacted unsaturated alcohol, transition metal catalyst, the organic alcohol coproduct derived from the reacted hydroperoxide, and solvent. Epoxy alcohols tend to be highly reactive and susceptible to decomposition at elevated temperatures, particularly in the presence of Lewis acids such as the transition metal compounds typically used as catalysts in epoxidation reactions.

Moreover, the methods developed to date for the asymmetric epoxidation of unsaturated substrates are not completely stereoselective. That is, both possible stereoisomers of the epoxy alcohol are generated, yielding a reaction product having an enantiomeric excess less than the maximum theoretically possible. Since the physiological activities of the epoxy alcohol product and its derivatives are generally directly related to optical purity, it is highly desirable to obtain a chiral epoxy alcohol having an enantiomeric excess as close as possible to 100%. Conventional physical methods of separation such as fractional distillation, fractional crystallization, extraction, and the like are normally not particularly effective in separating enantiomers either because the optical isomers have very similar physical properties (e.g., solubility, boiling point, melting point) or because of uneconomical losses during purification. Clearly, there is a need for a practical method whereby a chiral epoxy alcohol having enhanced optical purity may be efficiently recovered from an epoxidation reaction mixture.

SUMMARY OF THE INVENTION

This invention provides a method for purifying an epoxidation reaction mixture containing a major amount of a first chiral epoxy alcohol and a minor amount of a second chiral epoxy alcohol which is an enantiomer of the first chiral epoxy alcohol. The method comprises the steps of a) reacting the mixture with a carboxylic acid derivative selected from the group consisting of enol esters, saturated esters, and carboxylic acids and a lipase enzyme in amounts and under conditions effective to preferentially convert the second chiral epoxy alcohol to an epoxy ester, and b) separating the first chiral epoxy alcohol from the epoxy ester. Alternatively, the hydroxyl functionality of the first chiral epoxy alcohol is reacted after step (a) and before step (b) with an amount of an electrophilic derivatization reagent effective to form a chiral epoxy alcohol derivative. The chiral epoxy alcohol derivative is then separated from the epoxy ester.

The effectiveness of this method was unexpected in view of the fact that the kinetic resolution of racemic mixtures of epoxy alcohols using lipase catalyzed transesterification proceeds with low efficiency. For example, treatment of racemic glycidol with porcine pancreas lipase and an enol ester gives the corresponding epoxy ester with an enantiomeric excess of only 39–54% [Wang et al, *J. Am. Chem. Soc.* 110,7200(1988)]

DETAILED DESCRIPTION OF THE INVENTION

The epoxidation reaction mixture to be purified by the process of this invention contains a major amount of a first chiral epoxy alcohol and a minor amount of a second chiral epoxy alcohol which is an enantiomer of the first chiral epoxy alcohol. That is, the amount of the first chiral epoxy alcohol is greater than the amount of the second chiral epoxy alcohol. More preferably, the epoxidation reaction mixture has an enantiomeric excess of at least about 50%. Most preferably, the enantiomeric excess is at least about 75%. Percent enantiomeric excess is defined by the following formula:

$$\% \ e.e. = \frac{[\text{first chiral epoxy alcohol}] - [\text{second chiral epoxy alcohol}]}{[\text{first chiral epoxy alcohol}] + [\text{second chiral epoxy alcohol}]} \times 100$$

The epoxidation reaction mixture may be obtained by any method known in the art, including the asymmetric epoxidation of a prochiral unsaturated alcohol. A preferred method for the preparation of epoxidation reaction mixtures suitable for purification by the process of this invention is to react a prochiral unsaturated alcohol with an organic hydroperoxide in the presence of a chiral transition metal complex catalyst and an organic solvent. Preferably, the chiral transition metal complex catalyst is a titanium tetraalkoxide chiral carbinol complex catalyst. The unsaturated alcohol is preferably an allylic alcohol, although other unsaturated alcohols such as homoallylic alcohols are also suitable for use. Methods of this type are described in the following references: K. A. Jorgensen, *Chem. Rev.* 89, 431(1989); U.S. Pat. Nos. 4,471,130 and 4,764,628; European Pat. Nos. 197,766, 70,618, and 255,379; A. Pfenninger *Synthesis* 89(1986); Y. Gao et al *J. Am. Chem. Soc.* 109, 5765(1987); T. Katsuki et al *J. Am. Chem. Soc.* 102, 5974(1980); M. G. Finn et al in *Asymmetric Synthesis* Morrison, J. E., Ed., Academic Press, New York (1985), Vol. 5, Chapter 8, 247; B. E. Rossiter in *Asymmetric Synthesis* Morrison, J. D., Ed., Academic Press, New York (1985), Vol. 5, Chapter 7, 193. The teachings of these patents and papers are incorporated herein by reference in their entirety.

The epoxidation reaction mixture may alternatively be generated by asymmetric epoxidation of a prochiral unsaturated alcohol using a chiral organic hydroperoxide as described in copending U.S. application Ser. No. 07/386,655 (filed Jul. 27, 1989).

The chiral epoxy alcohols suitable for purification by the process of this invention include organic compounds having at least one epoxy functionality and at least one alcohol functionality. For example, 2,3-epoxy alcohols as well as 3,4-epoxy alcohols may be purified using this method. The method of this invention is particularly useful for the purification of epoxidation reaction mixtures of chiral epoxy alcohols having the general structure.

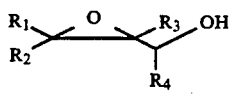

wherein $R_1$, $R_2$, $R_3$, and $R_4$ are the same or different and are independently selected from the group consisting of hydrogen, $C_1$–$C_{18}$ linear, branched, or cyclic alkyl, aryl, or aralkyl. In a preferred embodiment, the chiral epoxy alcohols are enantiomers of a water soluble epoxy alcohol such as glycidol, 2-methyl-glycidol, or 3-methyl-glycidol. The first chiral epoxy alcohol is most preferably an (S) enantiomer. Other suitable epoxy alcohols include, but are not limited to, phenyl glycidol (3-phenyl-oxirane methanol), 3-(4-nitrophenyl) oxirane methanol, 3-(4-bromophenyl) oxirane methanol, 3-heptyloxirane methanol, 3-octyl oxirane methanol, 3-(benzyloxymethyl) oxirane methanol, 2-tetradecyloxirane methanol, 2-methyl-3-phenyloxirane methanol, 2-phenyloxirane methanol, 2,3-diphenyloxirane methanol, 3-naphthyloxirane methanol, 2-cyclohexyloxirane methanol, 1-phenyloxirane methanol, 3-phenyloxirane ethanol, 2-(4-methyl) oxirane methanol, 3-pentyloxirane methanol, 3-propyloxirane methanol, 2-propyloxirane methanol, 7-oxabicyclo[4.1.0] heptane-1-methanol, and 2,3-epoxy geraniol.

The lipase enzyme, which functions as a catalyst for the stereoselective transesterification reaction between the chiral epoxy alcohol present in minor amounts in the epoxidation reaction mixture and the enol ester, may be from an animal, vegetable, or microbial source. Lipase enzymes are enzymes capable of hydrolyzing carboxylic acid esters and include those enzymes classified as triacylglycerol acylhydrolases, fatty acid esterases, and carboxylic ester hydrolases. The lipase enzyme may, for example, be a pancreatic, pregastric, lipoprotein, gastric, liver, or milk lipase from an animal such as a calf, cow, goat, lamb, pig, or the like. Vegetable-derived lipase enzymes such as castor bean lipase, wheat germ lipase, or rice bran lipase are also suitable for use. Alternatively, microbial lipase enzymes may be employed which are obtained from microorganisms such as Candida, Rhizopus, Chromobacterium, Humicola, Staphylococcus, Penicillium, Propionibacterium, Pseudomonas, Geotrichum, Aspergillus, Mucor, or Torulopsis species. mixtures of lipase enzymes may also be employed.

Lipase enzymes suitable for use in the process of this invention are commercially available in the form of powdered solids. The purity of the lipase enzyme is not critical; the lipase enzyme may contain varying amounts of other substances such as proteins and sugars. Crude lipase enzyme preparations, which may be readily obtained at low cost, will generally be satisfactory for use in this invention. Preferably, however, the lipase enzyme preparation employed will contain the equivalent of from about 1 to 500,000 units of activity per milligram, based on the generally adapted standard of 1 unit releasing 1 micromole of fatty acid from olive oil substrate in 1 minute under standard conditions. According to these standard conditions, the olive oil is dispersed to form a 5% emulsion in a 5% aqueous emulsion of gum arabic containing 50 μm calcium chloride. The assay is carried out at a pH of 6.0 and a temperature of 37° C.

The optimum amount of lipase enzyme employed will vary depending on a number of factors, including the activity and purity of the particular lipase enzyme preparation, the reactivity of the chiral epoxy alcohol and the enol ester, the reaction temperature, and the concentration of reactants, but generally speaking will be an amount effective to catalyze reaction of the enol ester and second chiral epoxy alcohol to form the epoxy ester. Approximately $10^3$ to $10^8$ units of lipase enzyme activity per mole of total epoxy alcohol is normally preferred to attain a practical reaction rate. Typically, from about 0.1 to 50 percent by weight of the combined weight of the first and second chiral epoxy alcohols will be a sufficient quantity of the lipase enzyme.

Lipase enzymes immobilized or supported on an inert material, usually in finely divided or particulate form, may also be advantageously used. Suitable inert materials are well-known in the art and include, for example, carbon, cellulose, glass, diatomaceous earth, agarose, alumina, silica, hydroxylapatite, and synthetic polymer resins. Examples of immobilized lipase enzymes are described in Macrae, "Interesterification of Fats and Oils" *Stud. Org. Chem.* 22,195(1985). Immobilized enzymes in general are described in *Industrial Enzymology—The Application of Enzymes in Industry*, Chapter 4.21, p. 437(1983).

Also suitable for use in the process of this invention are porous supports such as "Sepharose" or "Chromosorb" (available from Sigma) impregnated with aqueous solutions of lipase enzymes. supported lipase enzymes of this type are described, for example, in Cambou et al J. Am. Chem. Soc. 106, 2687(1984).

The lipase enzyme employed should exhibit stereoselectivity in the transesterification reaction. That is, the lipase enzyme preferentially catalyzes the reaction of the minor chiral epoxy alcohol with the enol ester. The relative ratio of major chiral epoxy alcohol to minor chiral epoxy alcohol is thereby increased.

The carboxylic acid derivative, which functions as an esterification agent, may be selected from the group consisting of enol esters, saturated esters, and carboxylic acids. It is preferred that the carboxylic acid derivative be an enol ester.

Enol esters suitable for use in this invention include compounds yielding a carboxylic acid and a ketone or aldehyde upon hydrolysis. Particularly suitable for use are vinyl or isopropenyl esters of $C_1$–$C_6$ aliphatic monocarboxylic acids such as vinyl acetate, vinyl propionate, vinyl valerate, isopropenyl acetate, isopropenyl propionate, and isopropenyl valerate.

Suitable carboxylic acids include, for example, $C_1$–$C_{18}$ saturated aliphatic carboxylic acids such as acetic acid, propionic acid, butyric acid, hexanoic acid, octanoic acid, lauric acid, and octadecanoic. The use of linear carboxylic acids is preferred.

The carboxylic acid derivative may alternatively be a saturated ester such as ethyl acetate, methyl propionate, phenyl acetate, benzyl acetate, butyl acetate, isobutyl acetate, trichloroethyl acetate, trichloroethyl butyrate, trichlorethyl caprylate, or trichloroethyl laurate. It is preferred that the ester be a halogenated alkyl ester as the halogenated alcohol generated by the lipase-catalyzed reaction of the ester with the epoxy alcohol will generally be less nucleophilic and will thus have less tendency to undergo interesterification with the epoxy ester formed.

The amount of carboxylic acid derivative employed is not critical, but should be sufficient to convert the second chiral epoxy alcohol to an epoxy ester. Most preferably, from about 0.5 to 100 equivalents of enol ester per equivalent of the second chiral epoxy alcohol is employed. It is desirable to achieve at least 50% conversion of the second chiral epoxy alcohol, although higher conversion levels (i.e., >75%) are preferred. Preferably, less than about 25% (more preferably, less than about 10%) reaction of the first chiral epoxy alcohol takes place.

Optionally, an inert organic solvent or mixture of such solvents may be present in or added to the epoxidation reaction mixture. The chiral epoxy alcohol and enol ester, but not the lipase enzyme, are preferably soluble in the organic solvent. The solvent chosen should not deactivate the lipase enzyme. If the epoxidation reaction mixture is produced by asymmetric epoxidation of an allylic alcohol using an organic hydroperoxide and a chiral transition metal catalyst, the organic solvent is preferably selected from the group consisting of chlorinated hydrocarbons (e.g., methylene chloride, chloroform), aliphatic hydrocarbons (e.g., isooctane, cyclohexane, hexane) and aromatic hydrocarbons (e.g., benzene, toluene, xylene, cumene, ethyl benzene). In general, the preferred amount of solvent will be from about 1 to 10 parts by weight of solvent per 1 part by weight of total chiral epoxy alcohol. Preferably, no water other than the small amount which might be associated with the lipase enzyme is present during treatment of the epoxidation reaction mixture with the lipase and the carboxylic acid derivative.

The epoxidation reaction mixture, lipase enzyme, carboxylic acid derivative, and, if desired, organic solvent are preferably agitated together throughout the reaction to maintain a dispersion of the lipase enzyme, preferably in a closed vessel under an inert atmosphere. Alternatively, a fixed bed or fluid bed of the lipase enzyme, which can be in immobilized or supported form, is employed. The reactants are contacted at a temperature and for a period of time effective to react the second chiral epoxy alcohol, present in minor amounts, with the carboxylic acid derivative to form an epoxy ester. Generally, speaking, it is desirable to achieve at least about 50% conversion (more preferably, at least about 75% conversion) of the second chiral epoxy alcohol. Reaction temperatures of from about $-20°$ C. to 75° C. and reaction times of from about 15 minutes to 12 hours are typically sufficient.

Following treatment of the epoxidation reaction mixture with the lipase enzyme and the enol ester, the epoxy ester produced may then be separated from the desired first chiral epoxy alcohol. Any suitable separation method may be used. If the lipase enzyme is insoluble and if molecular sieves have been used in the epoxidation reaction mixture, these materials may be removed and recovered by filtration, centrifugation, decantation, or the like. A particular advantage of the method of this invention is that nearly all lipase enzymes are insoluble in common organic solvents and thus may be readily recovered and reused with little loss in activity. If the first chiral epoxy alcohol is water soluble, it may be separated from the epoxy ester produced by extracting the epoxy alcohol into an aqueous phase using water. The epoxy ester will tend to remain in the organic phase. Any allylic ester formed by the reaction of unreacted unsaturated alcohol in the epoxidation reaction mixture with the carboxylic acid derivative will also tend to remain in the organic phase. The first chiral epoxy alcohol can then be isolated from the aqueous phase by fractional distillation. Alternatively, if the first chiral epoxy alcohol is water insoluble, the first chiral epoxy alcohol may be recovered by direct fractional distillation or, if crystallizable, by crystallization from solution using an appropriate solvent.

The first chiral epoxy alcohol may also be reacted in situ (i.e., without isolation) after treating the epoxidation reaction mixture with the lipase enzyme and the carboxylic acid derivative. The chiral epoxy alcohol derivatives obtained in this manner have widespread synthetic utility as chiral building blocks. The hydroxyl functionality of the first chiral epoxy alcohol is reacted with an effective amount of an electrophilic derivatization reagent. Preferred electrophilic derivatization reagents include, but are not limited to, carboxylic acid halides (e.g., p-nitrobenzoyl chloride, acetyl bromide, caprylyl chloride, naphthoyl chloride), organic sulfonyl halides (e.g., p-toluene sulfonyl chloride, methane sulfonyl chloride, nitrobenzene sulfonyl chloride, phenacyl sulfonyl chloride, p-bromo-benzene sulfonyl chloride, trifluoromethane sulfonyl chloride), organic silyl halides (e.g., tert-butyldiphenyl silyl chloride, trimethyl silyl chloride, tert-butyldimethyl silyl chloride), and carboxylic acid anhydrides (e.g., acetic anhydride). The molar ratio of electrophilic reagent:first chiral epoxy alcohol is preferably from about 0.1:1 to 10:1.

If the electrophilic derivatization reagent employed is a halide or anhydride, it is preferred to also add a tertiary amine such as triethylamine or another organic or inorganic base to the mixture to remove any acid generated during derivatization. The molar amount of base present should be approximately one to three times the molar quantity of derivatization reagent. Reaction temperatures of from about $-30°$ C. to $+80°$ C. are generally sufficient; at these temperatures, the derivatization may be effectively completed after about 5 minutes to 10 hours. The chiral epoxy alcohol derivative may then be separated from the epoxy ester by any appropriate method such as crystallization, distillation, extraction, or chromatography.

Without further elaboration, it is believed that one skilled in the art can, using the preceding description, utilize the present invention to its fullest extent. The following examples, therefore, are to be considered as merely illustrative and not limitative of the claims or remainder of the disclosure in any way whatsoever.

EXAMPLE 1

This example illustrates the purification of an epoxidation reaction mixture containing enantiomers of 3-methyl glycidol using the process of this invention. A mixture of crotyl alcohol (36 g; 0.50 mole), L(+)-diisopropyl tartrate (7.8 g; 0.033 mole), activated 3A molecular sieves (20 g), and methylene chloride (230 g was cooled to $-15°$ C. and then treated with titanium isopropoxide (7.8 g; 0.027 mole). After 15 minutes at $-15°$ C., cumene hydroperoxide (105 g of an 80% solution in cumene; 0.55 mole) was added over a period of 15 minutes. After 4 hours at a temperature of $-10°$ to $-15°$ C., complete conversion of the crotyl alcohol had been achieved (as determined by GC analysis). Lipase enzyme (10 g of P-30 Pseudomonas lipase from Amano Pharmaceutical Co.) and vinyl acetate (40 g; 0.46 mole) were then added. The reaction mixture was warmed to 0° C. and stirred at that temperature for 4 hours. GC analysis indicated that approximately 25% 3-methyl glycidol conversion had taken place. The molecular sieves and lipase enzyme were removed by filtration; the filtrate was extracted with 200 g water. Pure (S)-3-methyl glycidol was recovered by fractional distillation from the aqueous phase after removal of the water. The enantiomeric excess was found to be 100% by the Mosher ester method; no (R)-3-methyl glycidol was detected.

COMPARATIVE EXAMPLE 2

The procedure of Example 1 was repeated but without addition of the lipase enzyme. The e.e. of the 3-methyl glycidol product obtained was only 89%, demonstrating the advantages of the purification method of this invention.

EXAMPLE 3

The procedure of Example 1 was repeated using allyl alcohol as the unsaturated substrate in the epoxidation step. The e.e. of the isolated (S)-glycidol product was 96%, as compared to only 88% e.e. without use of the lipase enzyme.

EXAMPLE 4

The procedure of Example 1 was repeated using methallyl alcohol as the unsaturated substrate in the epoxidation step. The e.e. of the isolated (S)-2-methyl glycidol product was 97%, as compared to only 89% e.e. without use of the lipase enzyme.

EXAMPLE 5

A mixture of 4A molecular sieves (30 g) and 3000 g toluene is cooled to 0° C. L-(+)-Diethyl tartrate (97 g; 0.47 mole) and titanium butoxide (108.9 g; 0.32 mole) are added sequentially. After cooling the mixture to −20° C., tert-butyl hydroperoxide (3845 g of a 30% solution in octane; 12.8 moles) is added and the resulting mixture stirred for 20 minutes before adding freshly distilled cinnamyl alcohol (858.8 g; 6.4 moles) over a period of 2 hours. After 3 hours at −20° C., lipase enzyme (85 g of porcine pancreas lipase from Sigma; approximately 20,000–50,000 units activity per mg) and isopropenyl propionate (73 g; 0.64 mole) are added. The reaction mixture is warmed to +20° C. and stirred at that temperature for 8 hours. The reaction mixture is filtered to recover the molecular sieves and the lipase enzyme and then quenched with 10% aqueous sodium hydroxide saturated with sodium chloride. After stirring for 15 minutes, magnesium sulfate and diatomaceous earth are added. The mixture is then filtered and the unreacted hydroperoxide and solvent removed under reduced pressure to yield an oil. Recrystallization of the oil from petroleum ether/ethyl ether is expected to give a high yield of crystalline (2-S-trans)-3-phenyloxirane methanol having an e.e. of close to 100%.

EXAMPLE 6

A mixture of geraniol (1542.5 g; 10.0 moles), (+)-dibutyltartramide (338.0 g; 1.3 mole), zirconium tetrapropoxide (271.0 g; 1.0 mole), ethyl benzene hydroperoxide (2760 g; 20.0 mole), and isooctane (5000 g) is stirred at 0° C. for 20 hours. Immobilized lipase enzyme prepared by dispersing *Rhizopus delemar* lipase on diatomaceous earth as described in Tanaka et al *Agric. Biol. Chem.* 45,2387(1981) is then added and stirring continued for another 10 hours at +10° C. The immobilized lipase is removed by filtration before quenching the reaction mixture following the procedure described in Example 5. Solvent is removed from the filtrate under vacuum at low temperature before distilling the 2,3-epoxygeraniol product using a Kugelrohr apparatus. The 2,3-epoxygeraniol thus obtained is expected to have an e.e. of close to 100%.

EXAMPLE 7

This example illustrates the usefulness of the process of this invention in the preparation of chiral cis-epoxy alcohols having exceptionally high optical purity. A mixture of cis-2-penten-1-ol (5.0 g; 0.058 mol), L(+)-diiso-propyltartrate (0.084 g; 0.0036 mol), activated 3A molecular sieves (5 g), and methylene chloride (200 g) was cooled to −15° C. and then treated with titanium isopropoxide (0.084 g; 0.003 mol). After 15 minutes at −15° C., cumene hydroperoxide (20 g of an 80% solution cumene; 0.105 mol) was added over a period of 5 minutes. After 8 hours at −10° C. complete conversion of the cis-2-penten-1-ol was achieved (as determined by GC analysis). Lipase enzyme (1.5 g of P-30 Pseudomonas lipase from Amano Pharmaceutical Co.) and vinyl acetate (3.5 g; 0.04 mol) were added, and the resulting solution kept at 5° C. for 4 hours. The lipase enzyme and molecular sieves were removed by filtration and the filtrate worked up to recoverr the cis-epoxy alcohol product. The % e.e. of the (2-S-cis)-3-ethyloxirane methanol thus obtained was 92% (determined using a "Chiraldex" GC column).

When the reaction was repeated without the use of the lipase enzyme, the % e.e. of the cis-epoxy alcohol product was only 83%.

EXAMPLE 8

Asymmetric epoxidation of cis-2-butene-1,4-diol monobenzyl ether is carried out in accordance with the procedure of Example 1 of U.S. Pat. No. 4,900,847. After 3 days, the epoxidation reaction mixture is treated with 100,000 units of Pseudomonas lipase (SAM-2 lipase from Amano Pharmaceutical Co.) per mole of the epoxy alcohol. After 10 hours at 20° C., the chiral epoxy alcohol product is recovered from the reaction mixture in accordance with the procedures of U.S. patent application Ser. No. 07/420,859 (filed Oct. 11, 1989). The enantiomeric excess of the recovered product is expected to be significantly higher than the 85% e.e. value obtained in the absence of the lipase enzyme.

EXAMPLE 9

This example demonstrates the use of a saturated ester in the process of this invention.

The procedure of Example 1 is repeated using 54.8 g (0.25 mole) trichloroethyl butyrate as the carboxylic acid derivative in place of the vinyl acetate.

EXAMPLE 10

The use of a carboxylic acid in the process of this invention is illustrated by this example. The procedure of Example 3 is repeated using 70.1 g (0.35 mole) lauric acid as the carboxylic acid derivative in place of the vinyl acetate and 2.0 g of "Lipase My" (a crude *Can-*

*dida cylindracea* lipase available as a commercial product from Meito Sangyo Co.)

EXAMPLE 11

This example demonstrates the in situ derivatization of a chiral epoxy alcohol using the process of this invention. The procedure of Example 3 is repeated except after adding the lipase enzyme and the vinyl acetate and allowing the reaction mixture to stir for 4 hours at 0° C.;, the mixture is treated with triethylamine (61.5 g; 0.60 mole) and a solution of p-nitrobenzoyl chloride (92.8 g; 0.50 mole) in 125 mL methylene chloride and stirred for another hour at 0° C.

After filtering through a pad of diatomaceous earth, the filtrate is washed with 10% aqueous tartaric acid (2×125 mL), saturated $NaHCO_3$ (3×125 mL), and brine (2×125 mL). The organic phase is dried over $Na_2SO_4$, filtered through a small pad of silica gel, and concentrated to an oil (first at 12 mm Hg and then at 0.2 mm Hg at 60° C.). The oil is recrystallized from diethylether to give a high yield of (R)-oxirane methanol 4-nitrobenzoate having an e.e. of close to 100%.

EXAMPLE 12

The procedure of Example 11 is repeated, but using an equivalent amount of p-toluenesulfonyl chloride (95.3 g; 0.50 mole) in place of p-nitrobenzoyl chloride as the electrophilic derivatization reagent. (R)-Oxiranemethanol 4-methylbenzene sulfonate is obtained in high optical purity.

EXAMPLE 13

The procedure of Example 11 is repeated, but using methallyl alcohol (36.1 g; 0.50 mole) and t-butyldimethyl silyl chloride (90.4 g; 0.60 mole) in place of allyl alcohol and p-nitrobenzoyl chloride. The oil recovered by removal of the solvent from the washed organic layer is fractionally distilled (0.25 mm Hg; 41°–42° C.) to yield (2S-trans)-3-methyl oxiranemethanol t-butyldimethyl silyl ether in high optical purity.

I claim:

1. A method for enhancing the optical purity of an asymmetric epoxidation reaction mixture containing a first chiral epoxy alcohol selected from the group consisting of (S)-glycidol, (S)-2-methyl-glycidol and (S)-3-methyl glycidol, a second chiral epoxy alcohol which is an enantiomer of the first chiral epoxy alcohol, titanium tetraalkoxide chiral carbinol complex catalyst, and an organic alcohol coproduct, wherein the enantiomeric excess of the first chiral epoxy alcohol relative to the second chiral epoxy alcohol is at least about 50%; said method comprising the steps of:
   a) reacting the epoxidation mixture at a temperature of from about −20° C. to 75° C. with a carboxylic acid derivative selected from the group consisting of enol esters, saturated esters and carboxylic acids by using a lipase selected from the group consisting of pancreatic lipases, lipoprotein lipases and microbial lipases to preferentially convert at least about 50% of the second chiral epoxy alcohol to an epoxy ester while reacting less than about 25% of the first chiral epoxy alcohol; and
   b) separating the first chiral epoxy alcohol from the epoxy ester.

2. The method of claim 1 wherein the carboxylic acid derivative is an enol ester and wherein said enol ester is a vinyl or isopropenyl ester of a $C_1$–$C_6$ aliphatic monocarboxylic acid.

3. The method of claim 1 wherein the carboxylic acid derivative is an enol ester selected from the group consisting of vinyl acetate, vinyl propionate, vinyl valerate, isopropenyl acetate, isopropenyl propionate, and isopropenyl valerate.

4. The method of claim 1 wherein the epoxidation reaction mixture contains an inert organic solvent.

5. The method of claim 1 wherein reaction step (a) is carried out for a period of time of from about 15 minutes to 12 hours.

6. The process of claim 1 wherein the first chiral epoxy alcohol is water-soluble and is separated from the epoxy ester in step (b) by contacting the epoxidation reaction mixture with water so as to extract the first chiral epoxy alcohol into an aqueous phase.

* * * * *